US006752947B1

(12) United States Patent
Lanigan et al.

(10) Patent No.: US 6,752,947 B1
(45) Date of Patent: Jun. 22, 2004

(54) METHOD AND APPARATUS FOR THERMAL BONDING HIGH ELONGATION NONWOVEN FABRIC

(75) Inventors: William Robert Lanigan, Atlanta, GA (US); Richard J. Legare, Conyers, GA (US); Shiv Sibal, Conyers, GA (US)

(73) Assignee: Hercules Incorporated, Wilmington, DE (US)

( * ) Notice: Subject to any disclaimer, the term of this patent is extended or adjusted under 35 U.S.C. 154(b) by 484 days.

(21) Appl. No.: 09/116,371

(22) Filed: Jul. 16, 1998

(51) Int. Cl.[7] .............................. D01D 5/16; D01D 5/34
(52) U.S. Cl. ............ 264/172.18; 264/126; 264/172.15; 264/172.17; 264/175; 156/209; 156/292; 156/553; 156/583.1
(58) Field of Search ........................... 264/126, 172.15, 264/172.17, 172.18, 175; 156/209, 292, 553, 583.1

(56) References Cited

U.S. PATENT DOCUMENTS

| 1,945,024 A | 1/1934 | Coil et al. ................... 162/116 |
| 1,958,050 A | 5/1934 | Koppelman ................. 162/116 |
| 2,352,194 A | 6/1944 | Grabec ........................ 264/156 |
| 2,464,301 A | 3/1949 | Francis, Jr. ................. 428/167 |
| 3,081,514 A | 3/1963 | Griswold .................... 442/337 |
| 3,323,983 A | 6/1967 | Palmer et al. .............. 162/362 |
| 3,616,157 A * | 10/1971 | Smith ......................... 161/124 |
| 3,855,046 A | 12/1974 | Hansen et al. ............. 428/198 |
| 3,868,287 A | 2/1975 | Lewyckyj ................... 156/201 |
| 3,949,128 A | 4/1976 | Ostermeier ................. 428/152 |
| 4,110,152 A | 8/1978 | Dunning et al. ........... 156/553 |
| 4,248,822 A | 2/1981 | Schmidt ..................... 264/154 |
| 4,278,482 A | 7/1981 | Poteet et al. ................ 156/78 |
| 4,333,979 A | 6/1982 | Sciaraffa et al. ........... 428/179 |
| 4,374,888 A | 2/1983 | Bornslaeger ............... 428/198 |
| 4,419,160 A | 12/1983 | Wang et al. ............... 156/73.2 |
| 4,422,837 A | 12/1983 | Rasmussen ................ 425/289 |
| 4,443,512 A | 4/1984 | Delvaux .................... 428/162 |
| 4,473,432 A | 9/1984 | Leader et al. ............. 156/582 |
| 4,483,728 A | 11/1984 | Bauernfeind .............. 156/209 |
| 4,493,868 A | 1/1985 | Meitner ..................... 428/171 |
| 4,614,632 A | 9/1986 | Kezuka et al. ............ 264/280 |
| 4,626,467 A | 12/1986 | Hostetter .................... 442/361 |
| 4,741,944 A | 5/1988 | Jackson et al. ............ 428/152 |
| 4,817,788 A | 4/1989 | Bedenk et al. ............. 206/5 |
| 4,902,366 A | 2/1990 | Bader ......................... 156/296 |
| 4,938,832 A | 7/1990 | Schmalz ..................... 156/308.8 |
| D311,997 S | 11/1990 | Legare ........................ D5/53 |
| D313,319 S | 1/1991 | Legare ........................ D5/53 |
| D314,672 S | 2/1991 | Legare ........................ D5/53 |
| D314,673 S | 2/1991 | Legare ........................ D5/53 |
| 5,036,758 A | 8/1991 | Kobayashi et al. ......... 101/28 |
| 5,057,357 A | 10/1991 | Winebarger ............... 428/195 |
| 5,128,193 A | 7/1992 | Anapol et al. ............. 428/171 |
| 5,156,863 A | 10/1992 | Pricone et al. ............ 425/363 |
| 5,158,819 A | 10/1992 | Goodman, Jr. et al. ... 428/131 |
| 5,281,378 A | 1/1994 | Kozulla ....................... 264/83 |
| 5,296,289 A | 3/1994 | Collins ........................ 428/198 |
| 5,318,735 A | 6/1994 | Kozulla ....................... 264/83 |
| 5,383,778 A | 1/1995 | Schulz ........................ 425/363 |
| 5,403,426 A | 4/1995 | Johnson et al. ............ 156/256 |
| 5,431,994 A | 7/1995 | Kozulla ....................... 442/401 |
| 5,534,208 A | 7/1996 | Barr et al. .................. 264/160 |
| 5,540,953 A | 7/1996 | Harrington ................ 427/393.5 |
| 5,580,423 A | 12/1996 | Ampulski et al. ......... 162/117 |
| 5,620,776 A | 4/1997 | Schulz ........................ 428/156 |
| 5,622,734 A | 4/1997 | Clark et al. ................ 425/517 |
| 5,629,080 A | 5/1997 | Gupta et al. ............... 428/373 |
| 5,656,132 A | 8/1997 | Farrington, Jr. et al. ... 162/117 |
| 5,705,119 A | 1/1998 | Takeuchi et al. .......... 264/464 |
| 5,882,562 A | 3/1999 | Kozulla ....................... 264/83 |
| 5,985,193 A | 11/1999 | Harrington et al. ........ 264/83 |

FOREIGN PATENT DOCUMENTS

| EP | 0486158 | 5/1992 |
| EP | 0552013 | 7/1993 |
| EP | 0630996 | 12/1994 |
| EP | 0719879 | 7/1996 |
| FR | 2411260 | 7/1979 |
| WO | 97/37065 | 10/1997 |
| WO | WO97/37065 | * 10/1997 |
| WO | 98/15685 | 4/1998 |

OTHER PUBLICATIONS

Hercules Engraving Pattern 010.
Hercules Engraving Pattern 018.
Hercules Engraving Pattern 011–With Logo.
Hercules Bonding Pattern 004.
Overbeck & Co., Design No. 1174.
Overbeck & Co., Design No. 1557.
Overbeck & Co., Design No. 6080.
Overbeck & Co., Design No. 2586.
Overbeck & Co., Design No. 3388.
Overbeck & Co., Design No. 3780.
Overbeck & Co., Design No. 3933.
Overbeck & Co., Design No. 2403.
Overbeck & Co., Design No. 4759.
Overbeck & Co., Design No. 776.
Overbeck & Co., Design No. 982.
Trent et al., in *Macromolecules*, vol. 16, No. 4; 1983; "Ruthenium Tetroxide Staining of Polymers for Electron Microscopy".

(List continued on next page.)

*Primary Examiner*—Terrel Morris
*Assistant Examiner*—John J. Guarriello
(74) *Attorney, Agent, or Firm*—David Edwards

(57) ABSTRACT

A method of forming a thermally bonded, nonwoven polypropylene fabric is provided and includes passing a web of thermally bondable skin-core polypropylene fibers through a calender nip under heat and pressure to produce a nonwoven fabric having elongation. The patterned calender roll is embossed with a plurality of spaced and staggered lands particularly dimensioned, configured and oriented to provide the desired bonding spot size and spacing between the bonding spots such that when utilized in the calender roll, an improved soft polypropylene fabric or cover sheet having a high elongation results.

26 Claims, 7 Drawing Sheets

U.S. PATENT DOCUMENTS

"Cut strip test" in ASTM D–1682–64 (Re–Appproved 1975), pp. 255–260.
American National Standard, Standard Test Methods for Breaking Load and Elongation of Textile Fabrics[1], ASTM D–1682–64 (Reapproved 1975), pp. 255–260.

Legare, R.J., 1986 TAPPI, *Synthetic Fibers for Wet System and Thermal Bonding Applications*, Boston Park Plaza Hotel & Towers, Boston, Mass., Oct. 9–10, 1986, " Thermal Bonding of Polypropylene Fibers in Nonwovens", pp. 1–13 and attached Tables and Figures.

* cited by examiner

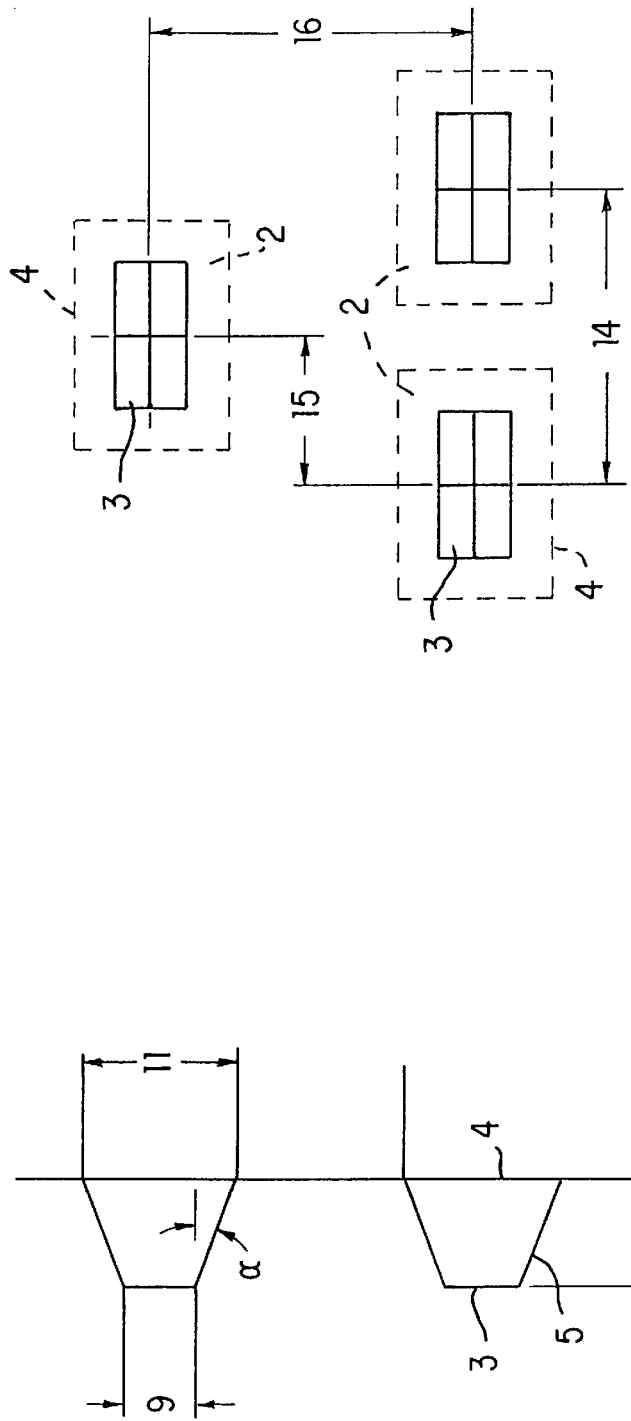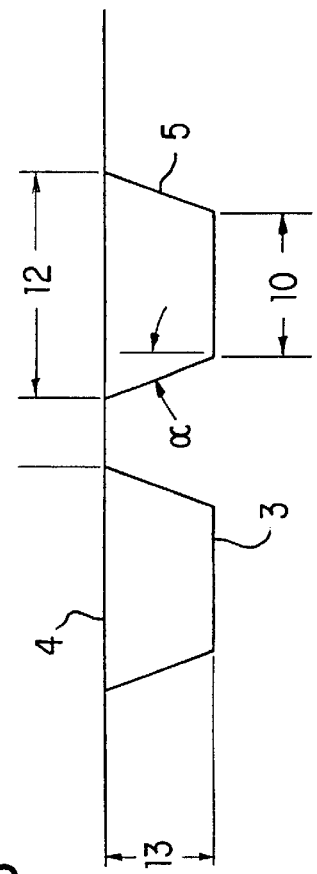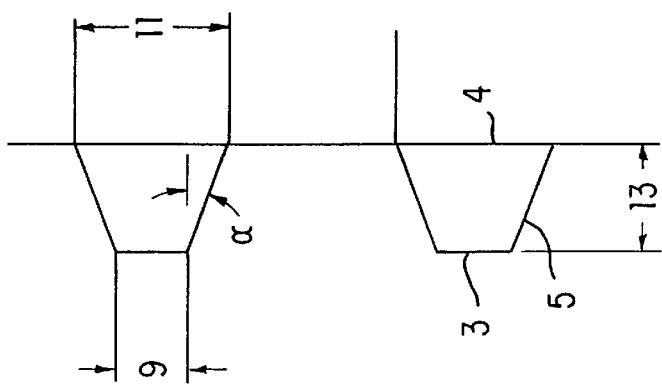

METHOD AND APPARATUS FOR THERMAL BONDING HIGH ELONGATION NONWOVEN FABRIC

BACKGROUND OF THE INVENTION

1. Field of the Invention

The present invention relates to thermal bonding of nonwoven fabric, especially high elongation nonwoven fabric, and to calender rolls for producing such nonwoven fabric as well as to nonwoven fabrics and articles including nonwoven fabrics.

2. Description of Background Information

Nonwoven fabrics are typically made by making a web, and then thermally bonding the fibers together. For example, staple fibers can be converted into nonwoven fabrics using, for example, a carding machine, and the carded fabric can be thermally bonded. The thermal bonding can be achieved using various heating techniques, including heating with heated rollers, hot air and heating through the use of ultrasonic welding.

When heated rollers are utilized to bond the carded fabric, typically there is utilized one roll that is smooth and a calender roll that includes bonding spots thereon. The material to be thermally bonded is fed through a nip between the smooth roll and the calendar roll, with sufficient heat being applied to obtain thermal bonding of the material.

Conventional thermal bonding calender rolls, such as embossed calender rolls, are configured with a plurality of lands to provide bonding spots to provide maximum machine direction strength and cross direction strength, while preferably providing a soft feel or touch to the material, especially when forming the thermal bonded material or fabric from synthetic materials. Such thermal bonded fabric is often used to form nonwoven cover stock, which is typically used for hygiene products, such as a top sheet of a diaper. In such applications, one face or side of the cover stock material is placed in contact with a human body, for example, placed on the skin of a baby. Therefore, it is desirable that the face in contact with the human body exhibit softness.

The conventional processes utilize embossed thermal bonding calender rolls designed with a plurality of spaced lands that form bonding spots to provide a soft touch, as well as maximum machine direction and cross-direction strength. However, most of the prior art card-produced nonwoven fabrics do not have acceptable stretch characteristics.

There is therefore a need to produce nonwoven fabric having a high degree of elongation, especially with acceptable strength.

SUMMARY OF THE INVENTION

Accordingly, it is an object of the present invention to provide improved methods of manufacturing thermal bonded, nonwoven, fibrous web materials of high elongation, preferably with acceptable strength.

It is also an object of the present invention to provide a thermal bonding calender roll that will produce thermally bonded nonwoven material with high stretch or elongation.

The present invention provides a method of manufacturing thermally bonded fabric having high elongation, comprising forming a web of thermally bondable polypropylene fibers; passing the web over a heated calender roll having a patterned surface including a plurality of rows of lands, with each of the lands having an upper surface, with upper surfaces of lands in adjacent rows being staggered such that they do not overlap one another in a machine direction; and thermally bonding the fibers at bond points located about the upper surfaces of the lands such that fibers extending substantially in the machine direction will only have one bond point for adjacent rows.

The polypropylene fibers are preferably skin core polypropylene fibers.

The web can be provided as a carded fibrous web, or as a plurality of continuous filaments.

The elongation of the nonwoven fabric is at least about 120%, preferably greater than about 140%, more preferably greater than about 160%, even more preferably greater than about 180%, even more preferably greater than about 200%, even more preferably greater than about 250%, and most preferably greater than 300%.

The passing of the web over a heated calender roll can comprise passing the fibrous web between a pair of cooperating rolls in a calender nip, at least one of the pair of rolls having the patterned surface and comprising a cylindrical roll having an outer cylindrical surface including a plurality of lands; the lands being arranged on the outer cylindrical surface in a plurality of spaced apart rows; each of the lands comprising a tapered shape including a base, preferably substantially rectangular, tapering to an upper surface, which is preferably substantially rectangular; the upper surface including short sides oriented in the machine direction of about 0.036 cm to 0.066 cm in length, preferably about 0.043 cm to 0.059 cm, with a preferred value being about 0.051 cm, and long sides of about 0.071 cm to 0.133 cm in length oriented in a cross direction, preferably about 0.087 cm to 0.117 cm, with a preferred value being about 0.102 cm; adjacent rows of the lands being spaced apart a distance, with respect to the centers of the lands, of about 0.157 cm to 0.291 cm, preferably about 0.190 cm to 0.258 cm, with a preferred value being about 0.224; upper surfaces of lands in adjacent rows being staggered such that upper surfaces in adjacent rows do not overlap with one another in a machine direction providing a plurality of spaced apart bond points capable of bonding fibers extending substantially in the machine direction at only one bond point for adjacent rows; and the plurality of lands providing a bond area up to about 20%, preferably from about 5% to 20%, more preferably about 8% to 15%, even more preferably about 8% to 12%, with a preferred value being about 11%

The upper surfaces of the lands can be substantially rectangular. Moreover, the bases can overlap in the machine direction in adjacent rows.

Centers of the lands in each row are spaced apart by a distance of about 0.142 cm to 0.264 cm, preferably about 0.173 cm to 0.233 cm, with a preferred value being about 0.203 cm, and centers of the lands in adjacent rows are spaced apart by a distance of about 0.071 cm to 0.133 cm, preferably about 0.087 cm to 0.117 cm, with a preferred value being about 0.102 cm. The lands are constructed and arranged such that a straight fiber lying at an angle of greater than 15% with respect to the machine direction, more preferably about 35° to 55°, and even more preferably 45°, is positioned in a space between the lands, whereby the fiber is not be bonded.

The lands are preferably of a truncated pyramidal shape, preferably having substantially rectangular bases with short sides about 0.075 cm to 0.139 cm in length oriented in the machine direction, preferably 0.091 cm to 0.123 cm, with a preferred value being about 0.107 cm, and long sides about 0.111 cm to 0.205 cm in length oriented in the cross direction, preferably about 0.134 cm to 0.182 cm, with a preferred value being about 0.158 cm, and tapered side walls extending between the base and the upper surface at an angle a of about 14° to 35°, preferably about 17° to 26°, more preferably about 17° to 23°, with a preferred value being about 20°.

The lands can have a height of about 0.053 cm to 0.099 cm, preferably about 0.065 cm to 0.087 cm, with a preferred value being about 0.076 cm.

There is also provided a method of manufacturing thermally bonded fabric having high elongation, comprising forming a web comprising thermally bondable skin-core polypropylene fibers; passing the web over a calender roll having a patterned surface including a plurality of rows of lands, with each of the lands having an upper surface, with upper surfaces of lands in adjacent rows being staggered such that they do not overlap one another in a machine direction; applying heat and pressure to the fibrous web at a location of the calender roll to thermally bond the fibers at bond points located about the upper surfaces of the lands such that fibers extending substantially in the machine direction will only have one bond point for adjacent rows.

The present invention is also directed to the calender roll and to polypropylene fabrics formed by the methods.

BRIEF DESCRIPTION OF THE DRAWINGS

The above and other features and advantages of the present invention will be made apparent from the following description of the preferred embodiments, given as non-limiting examples, with reference to the accompanying drawings, in which:

FIG. 2 depicts the relative spacing of the lands forming the bond spots according to the present invention;

FIG. 3 depicts an end view of the lands of FIG. 1;

FIG. 4 depicts a side view of the lands of FIG. 1;

DETAILED DESCRIPTION OF THE PREFERRED EMBODIMENT

The present invention is directed to method and apparatus for thermal bonding high elongation nonwoven fabric, as well as the nonwoven fabric produced thereby, and articles including such nonwoven fabric.

The nonwoven fabric of the instant invention is composed of various forms of fibers, and within the scope of the present invention, include filaments and staple fibers. These terms are used in their ordinary commercial meanings. Typically, "filament" is used herein to refer to the continuous fiber on the spinning machine. "Staple fiber" is used to refer to cut fibers or filaments. Staple fiber is used in a multitude of products, such as personal hygiene, medical, industrial and automotive products and commonly ranges in length from about 5 mm to about 16 cm. Preferably, for instance, staple fibers for nonwoven fabrics useful in diapers have lengths about 2.5 cm to 7.6 cm, more preferably about 3.2 cm to 5 cm. Thicknesses of fiber or filament are measured in denier per filament (dpf), which is the weight in grams of 9,000 m (9 km) of filament. As a matter of convenience, "fiber" is herein also used to describe filament or staple fiber.

The calender roll according to the present invention is constructed and arranged to provide a lower degree of bonding area than usual as well as fewer bonding points on individual fibers. In particular, the lands are dimensioned and positioned on the calender roll to be sufficiently spaced apart such that there are a minimum number of fibers that may not be bonded. Moreover, the lands are spaced such that all, or substantially all, individual fibers oriented in the machine direction have bond points. Moreover, the lands should not be so distanced from each other that the strength properties, including machine direction strength and cross-directional strength, are rendered unacceptable. The lands should be constructed and arranged to provide fibers than are capable of sliding with respect to one another to thereby provide a highly stretchable fabric, especially while providing a fabric of sufficient strength characteristics.

Figure 1:
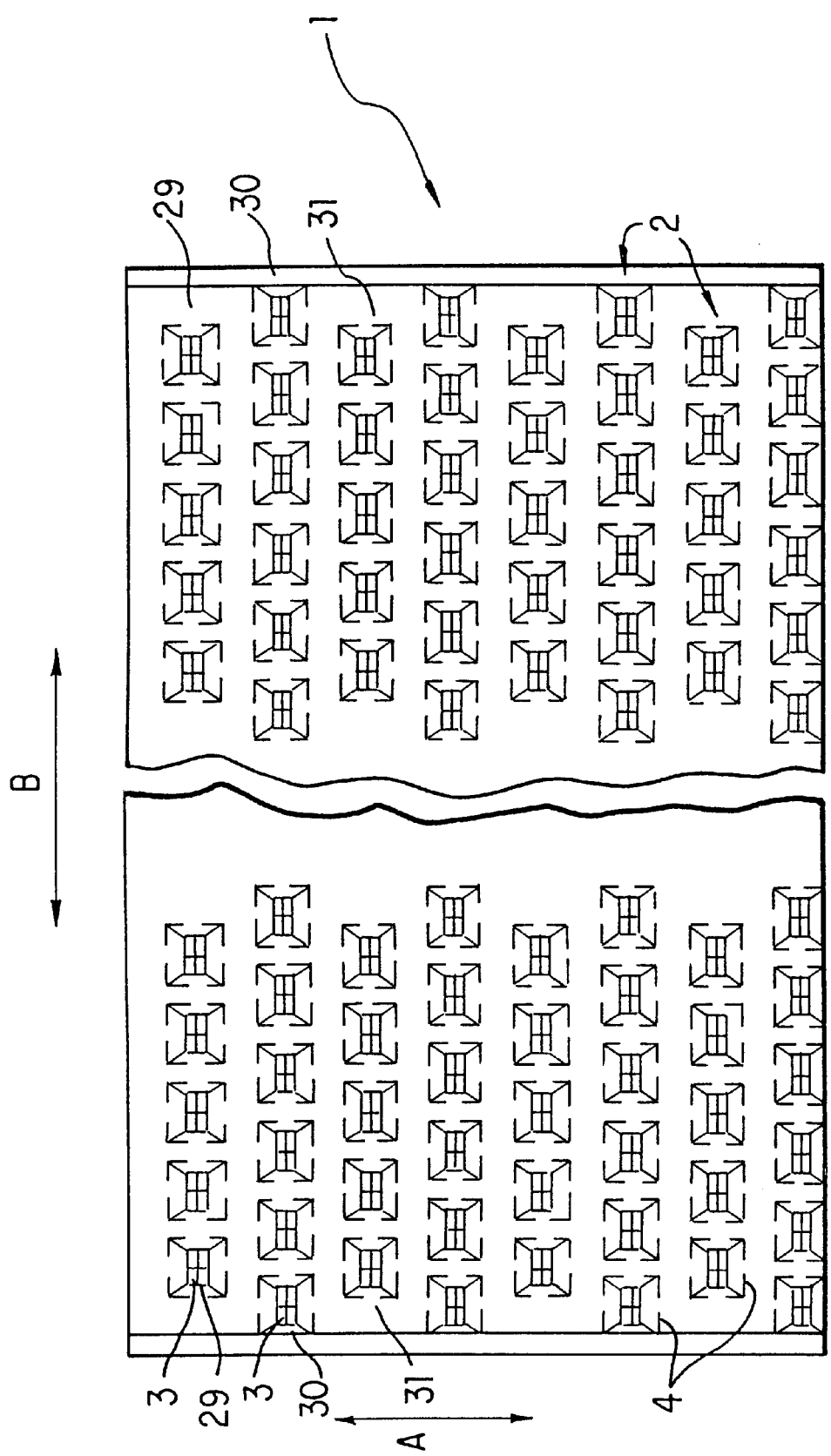
FIG. 1 depicts a portion of the patterned calender roll according to the present invention, with the pattern broken away at the central portion.

Moreover, as can be seen in FIG. 1, the lands in one row 29 are staggered with respect to lands in an adjacent row 30 so that there are a reduced number of bonding points, with bonding points occurring on alternating rows 29 and 31 of lands, at least for fibers oriented in the machine direction. In other words, fibers extending in the machine direction, or substantially in the machine direction, will only have one bonding point for each adjacent two rows, such as adjacent rows 29 and 30, and will have two bonding points for alternating rows, such as alternating rows 29 and 31.

Figure 11:
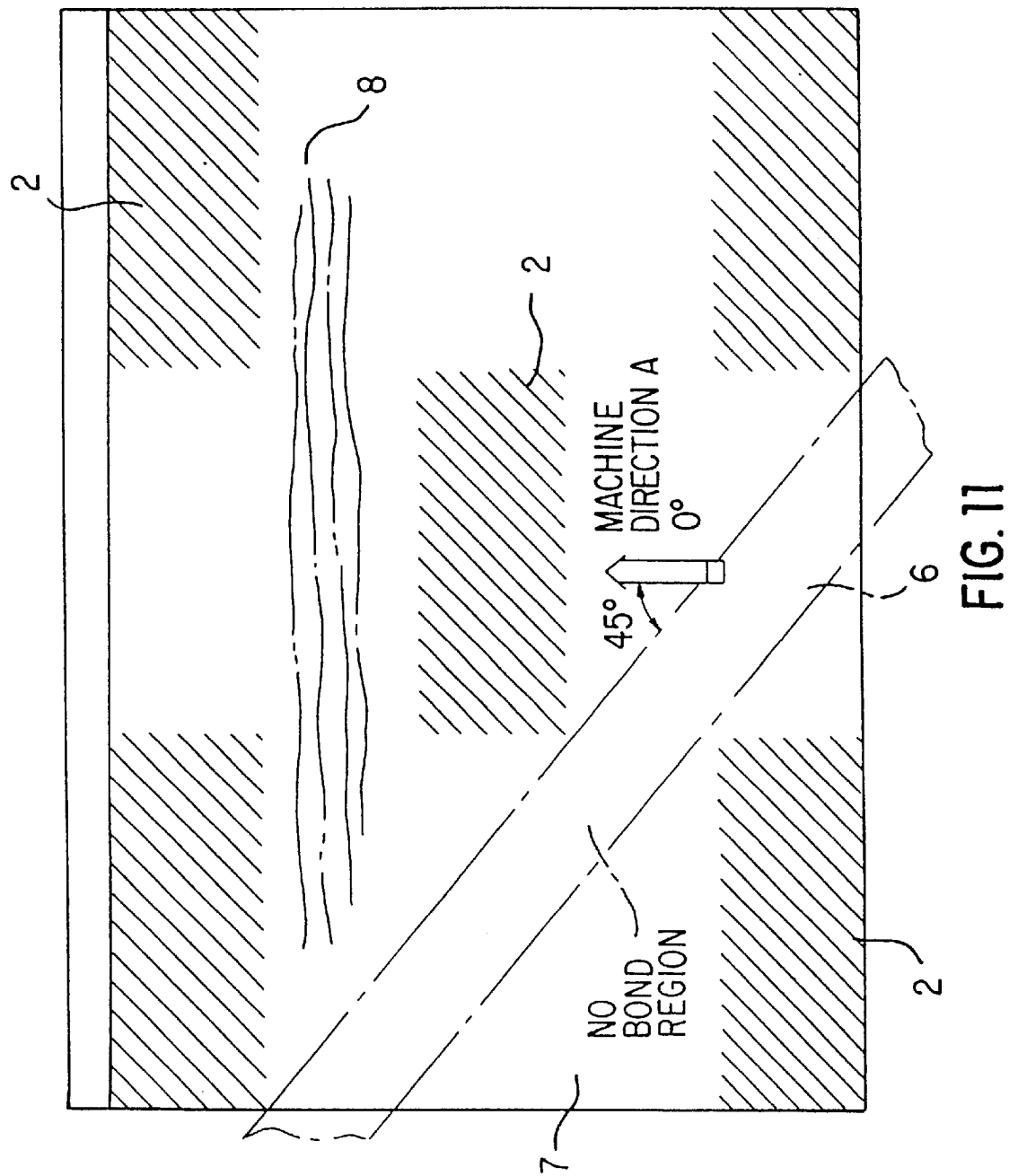
FIG. 11 is a schematic depiction of bonding regions of a calender roll according to the present invention.

Still further, with reference to FIG. 11, the lands on the calender roll are preferably constructed and arranged to ensure that bonding points are present on each fiber, except for fibers 6 that are oriented at an angle of greater than about 15° with respect to the machine direction, more preferably about 35° to 55°, with a preferred value being about 45°, with respect to the machine direction, and within the space 7 between lands, which will be a no bond region. The spacing between the rows of lands (in the machine direction) can be varied, but the spacing should not be increased to the extent the angle between lands in successive rows (in the machine direction) exceeds an angle of greater than about 15° with respect to the machine direction, more preferably about 35° to 55°, and most preferably an angle of about 45°.

It is noted that reference to angles of about 35° to 55°, as well as 45°, is being made primarily to assist an understanding of the spacing of the lands. For example, in practice, the likelihood that a fiber would be positioned at only about a 45° angle is practically zero. In this regard, it is noted that at least a major number of the fibers, and substantially all fibers, will be oriented in the machine direction. Moreover, fibers will not ordinarily align in a linear configuration.

Again, as noted above, by maintaining the relationships according to the present invention, bonding points will be present on substantially every fiber, except for fibers that are oriented at an angle of greater than about 15° with respect to the machine direction, more preferably about 35° to 55°, and preferably about 45°, with respect to the machine direction, and within the space 7 between lands, or fibers that are aligned substantially at an angle of 90° with respect to the machine direction, as illustrated at region 8, which also will not have bonding points. This will result in a fabric having fibers with a reduced number of bond points, thereby providing a highly stretchable fabric, especially while providing a fabric of sufficient strength characteristics.

Still further, the lands on the calender roll are constructed and arranged to provide a bond area which is in the range of about 5% to 20%, more preferably about 8% to 15%, even more preferably about 8% to 12%, with a particularly preferred bond area being about 11%.

With the calendar rolls of the present invention, the fibers can be processed on high speed machines for the making of various materials, in particular, nonwoven fabrics that can have diverse uses, including cover sheets, acquisition layers and back sheets in diapers. The fibers of the present invention enable the production of nonwoven materials at speeds as high as about 500 ft/min, more preferably as high as about 700 to 800 ft/min, and even as more preferably as high as about 980 ft/min (about 300 meters/min) or higher, such as about 350 meters/min, at basis weights from about 10 g/yd$^2$ (gsy) to 50 gsy, more preferably 20–40 gsy, and having cross-directional strengths, for a basis weight of about 20 gsy, on the order of at least about 200 g/in, more preferably 300 to 400 g/in, preferably greater than about 400 g/in, and more preferably as high as about 650 g/in, or higher. Further, the fabrics can have an elongation of about at least about 120%, more preferably at least about 140%, even more preferably at least about 160%, even more preferably at least about 180%, even more preferably at least about 200%, even more preferably at least about 250%, and even more preferably at least about 300%, and a toughness of about 600 to 2100 g/in, preferably about 1440–2100 g/in.

Turning to FIG. 1, a portion of a calender roll 1 is depicted illustrating a plurality of lands 2 that are configured to have a generally truncated pyramidal shape, and are arranged in parallel rows with the lands 2 in alternating rows being staggered. The calender roll 1 is formed as a cylindrical member which may have a diameter in the range of about 30 cm to 180 cm, preferably about 45 cm to 90 cm, and a face width in the range of about 45 cm to 450 cm, preferably about 50 cm to 400 cm, which includes the pattern of staggered lands 2 as shown in FIG. 1, such as by embossing, engraving, or by any method for forming lands on a calender rolls.

As shown in FIGS. 2–4, the upper surface 3 of each land preferably has a rectangular or substantially rectangular shape as shown, but can have other shapes as long as bonding spots can be attained. The width 9 of upper surface 3 aligned in the circumferential or machine direction (FIG. 1, arrow A) of the calender roll is in the range of about 0.036 cm to 0.066 cm, and preferably about 0.043 cm to 0.059 cm, with a preferred value being about 0.051 cm. The length 10 of the upper surface 3 aligned in the cross-direction (FIG. 1, arrow B) of the calender roll is about 0.071 cm to 0.133 cm, and preferably about 0.087 cm to 0.117 cm, with a preferred value being about 0.102 cm.

Also, as shown in FIGS. 2–4, the base 4 of each land preferably has a rectangular or substantially rectangular shape as shown, but can have other shapes as long as bonding spots can be attained. The width 11 of the base 4 aligned in the circumferential or machine direction of the calender roll is in the range of about 0.075 cm to 0.139 cm, and preferably about 0.091 cm to 0.123 cm, with a preferred value being about 0.107 cm. The length 12 of base 4 aligned in the cross-direction of the calender roll is in the range of about 0.111 cm to 0.205 cm, preferably about 0.134 cm to 0.182 cm, with a preferred value being about 0.158 cm, The lands have a height 13 of about 0.053 cm to 0.099 cm, and preferably about 0.065 cm to 0.087 cm, with a preferred value being about 0.076 cm. Side walls 5 have a taper α (as shown in FIGS. 3 and 4) in the range of about 14° to 35°, more preferably 14° to 26°, even more preferably about 17° to 23°, with a preferred value being about 20°.

As shown in FIG. 2, the centers of adjacent lands in a row are spaced apart a distance 14 in the range of about 0.142 cm to 0.264 cm, and preferably about 0.173 cm to 0.233 cm, with a preferred value being about 0.203 cm apart. The centers of lands in adjacent rows are spaced apart a distance 15 in the range of about 0.071 cm to 0.133 cm, and preferably about 0.087 cm to 0.117 cm, with a preferred value being about 0.102 cm apart. This results in an arrangement of the lands, as seen in FIG. 2, and the lands should be constructed and arranged whereby the upper surface 3 of the lands in adjacent, such as rows 29 and 30, and in the machine direction do not overlap. Moreover, the bases 4 are preferably constructed and arranged such that they overlap.

Expanding upon the above, the upper surface or central land area 3 of each land in a row, as can be seen in FIGS. 1 and 2, is dimensioned and positioned so as not to overlap with the upper surface or central land area 3 of lands in an adjacent row. However, as can also be seen in FIGS. 1 and 2, the base 4 of lands in one row will preferably overlap with bases 4 in an adjacent row. In particular, bases 4 positioned within a row will overlap with two bases 4 in an adjacent row, whereas bases 4 positioned at the end of a row will usually overlap only one base 4 in an adjacent row.

As also shown in FIG. 2, the centers of the lands between adjacent rows are spaced apart a distance 16 in the range of about 0.157 cm to 0.291 cm, and preferably about 0.190 cm to 0.258 cm, with a preferred value being about 0.224 cm.

The calender roll according to the present invention can be constructed with various materials, such as steel including ANSI 1030 or better engravable steel. Moreover, the lands can be formed in any manner, such as by etching.

The above-described patterned calender roll is utilizable in the method of the present invention which includes thermally bonding fibers together to form a nonwoven fabric utilizing the calendar roll to form bond spots in the nonwoven fabric. For example, heat and pressure can be applied to the web in the nip between the calender roll of the present invention and a smooth roll for thermally bonding the fibers with a pattern of lands that form bonding points. By applying heat and pressure in the calender nip, portions of the fiber are fused or melted together to form the bond points. The pressure and temperature will vary with the material of the web to be bonded. The temperature can range over a wide range of temperatures, such as from about 110° C. to 220° C. Preferably, wherein the fibers comprise polypropylene, the rolls are heated to a temperature of about 135° C. to 200° C., more preferably about 140° C. to 185° C., and even more preferably about 140° C. to 180° C., and apply a pressure of about 160 to 480 pounds per linear inch, more preferably about 180 to 300 pounds per linear inch, with a preferred valued being about 240 pounds per linear inch. The bond points and non-bonded areas contribute to the strength of the nonwoven material, as well as its softness, stretchability, and elongation properties.

The fibers useful in accordance with the present invention can comprise various polymers. Thus, polymers useful with the present invention can comprise various spinnable polymeric materials such as polyolefins and blends comprising polyolefins. Preferably, the polymer is a polypropylene or a blend comprising a polypropylene. The polypropylene can comprise any polypropylene that is spinnable. The polypropylene can to be atactic, heterotactic, syndiotactic, isotactic and stereoblock polypropylene—including partially and fully isotactic, or at least substantially fully isotactic—polypropylenes. Polypropylenes which may be spun in the inventive system can be produced by any process. For example, the polypropylene can be prepared using Zeigler-Natta catalyst systems, or using homogeneous or heterogeneous metallocene catalyst systems.

Further, as used herein, the terms polymers, polyolefins, polypropylene, polyethylene, etc., include homopolymers, various polymers, such as copolymers and terpolymers, and mixtures (including blends and alloys produced by mixing separate batches or forming a blend in situ). When referring to polymers, the terminology copolymer is understood to include polymers of two monomers, or two or more monomers, including terpolymers. For example, the polymer can comprise copolymers of olefins, such as propylene, and these copolymers can contain various components. Preferably, in the case of polypropylene, such copolymers can include up to about 20 weight %, and, even more preferably, from about 0 to 10 weight % of at least one of ethylene and butene. However, varying amounts of these components can be contained in the copolymer depending upon the desired fiber.

Further, the polypropylene can comprise dry polymer pellet, flake or grain polymers having a narrow molecular weight distribution or a broad molecular weight distribution, with a broad molecular weight distribution being preferred. The term "broad molecular weight distribution" is here defined as dry polymer pellet, flake or grain preferably having an MWD value (i.e., Wt.Av.Mol.Wt./No.Av.Mol.Wt. measured by SEC as discussed below) of at least about 5, preferably at least about 5.5, more preferably at least about 6. Without limiting the invention, the MWD is typically about 2 to 15, more typically, less than about 10.

The resulting spun melt preferably has a weight average molecular weight varying from about $3 \times 10^5$ to about $5 \times 10^5$, a broad SEC molecular weight distribution generally in the range of about 6–20 or above, a spun melt flow rate, MFR, (determined according to ASTM D-1238-86 (condition L;230/2.16), which is incorporated by reference herein in its entirety) of about 13 to about 50 g/10 minutes, and/or a spin temperature conveniently within the range of about 220°–315° C., preferably about 300° C.

Still further, the polypropylene can be linear or branched, such as disclosed by U.S. Pat. No. 4,626,467 to Hostetter, which is incorporated by reference herein in its entirety, and is preferably linear. Additionally, in making the fiber of the present invention, the polypropylene to be made into fibers can include polypropylene compositions as taught in Gupta et al. U.S. Pat. No. 5,629,080, and European Patent Application No. 0 552 013 to Gupta et al., which are incorporated by reference herein in their entireties. Still further, polymer blends such as disclosed in Kozulla, U.S. Pat. application Ser. No. 08/358,884, filed Dec. 19, 1994, and Kozulla, U.S. Pat. application Ser. No. 08/998,592, filed Dec. 29, 1997, and European Patent Application No. 0 719 879, which are incorporated by reference in their entireties, can also be utilized. Yet further, polymer blends, especially polypropylene blends, which comprise a polymeric bond curve enhancing agent, as disclosed in U.S. patent application Ser. No. 08/728,491, to Harrington et al. and WO 97/37065, incorporated by reference as if set forth in their entirety herein, can also be utilized.

The production of polymer fibers for nonwoven materials usually involves the use of a mix of at least one polymer with nominal amounts of additives, such as antioxidants, stabilizers, pigments, antacids, process aids and the like. Thus, the polymer or polymer blend can include various additives, such as melt stabilizers, antioxidants, pigments, antacids and process aids. The types, identities and amounts of additives can be determined by those f ordinary skill in the art upon consideration of requirements of the product. Without limiting the invention, preferred antioxidants include Irganox 1076, and Irgafos 168 (both from Ciba-Geigy, Tarrytown, N.Y.) which may typically be present in the polymer composition in amounts of about 50–150 ppm (Irganox 1076) or about 200–1000 ppm (Irgafos 168) based on the weight of the total composition. Other optional additives which can be included in the fiber of the present invention include, for example, pigments such as titanium dioxide, typically in amounts up to about 2 weight %, antacids such as calcium stearate, typically in amounts ranging from about 0.01–0.2 weight %, colorants, typically in amounts ranging from 0.01–2.0 weight %, and other additives.

Various finishes can be applied to the filaments to maintain or render them hydrophilic or hydrophobic. Also, one or more components can be included in the polymer blend for modifying the surface properties of the fiber, such as to provide the fiber with repeat wettability, or to prevent or reduce build-up of static electricity. Hydrophobic finish compositions preferably include antistatic agents. Hydrophilic finishes may also include such agents.

Preferable hydrophobic finishes include those of U.S. Pat. No. 4,938,832, European Patent Application No. 486,158, all to Schmalz, which are incorporated by reference as if set forth in their entireties herein. These documents describe fiber finish compositions containing at least one neutralized phosphoric acid ester having a lower alkyl group, such as a 1–8 carbon alkyl group, which functions as an antistat, in combination with polysiloxane lubricants.

Another hydrophobic finish composition that can be used with the present invention is disclosed in U.S. Pat. No. 5,403,426, to Johnson et al., incorporated by reference as if set forth in its entirety herein. This patent describes a method of preparing hydrophobic fiber for processing inclusive of crimping, cutting, carding, compiling and bonding. The surface modifier comprises one or more of a class of water soluble compounds substantially free of lipophilic end groups and of low or limited surfactant properties.

Yet another hydrophobic finish composition that can be used with the present invention is disclosed in U.S. patent application Ser. No. 08/728,490, filed Oct. 9, 1996, to Hirwe et al. and WO 98/15685, which are incorporated by reference as if set forth in their entirety herein. The hydrophobic finish compositions of these documents comprise hydrophobic esters of pentaerythritol homologs, preferably hydrophobic esters of pentaerythritol and pentaerythritol oligomers. Finish compositions comprising such a lubricant may further comprise other lubricants, anti-static agents, and/or other additives.

Further, U.S. Pat. No. 5,540,953, to Harrington, incorporated by reference as if set forth in its entirety herein, describes antistatic compositions useful in the preparation of hydrophobic fibers and nonwoven fabrics. One finish described therein comprises 1) at least one neutralized $C_3$–$C_{12}$ alkyl or alkenyl phosphate alkali metal or alkali earth metal salt, and 2) a solubilizer. A second finish described therein comprises at least one neutralized phosphoric ester salt.

Other ingredients that may comprise a finish composition useful with the present invention include emulsifiers or other stabilizers, and preservatives such as biocides. One preferred biocide is Nuosept® 95, 95% hemiacetals in water, available from Nuodex Inc. division of HULS America Inc. (Piscataway, N.J.).

Finish compositions comprising hydrophilic finishes or other hydrophobic finishes, may be selected by those of ordinary skill in the art according to the characteristics of the apparatus and the needs of the product being manufactured. Other additives such as antistatic agents, stabilizers, emulsifiers and preservatives may be similarly selected.

The fibers are preferably polypropylene fibers, and more preferably are polypropylene fibers formed as skin-core fibers.

Fibers without a skin-core structure can be prepared by providing conditions which result in the manufacture of fibers without a skin-core structure. Such conditions may be achieved, for example, by providing an environment that sufficiently avoids oxidation of the surface of the filaments.

Fibers with a skin-core structure can be produced by any procedure that achieves oxidation, degradation and/or lowering of molecular weight of the polymer blend at the surface of the fiber as compared to the polymer blend in an inner core of the fiber. Such a skin-core structure can be obtained, for example, through a delayed quench and exposure to an oxidative environment, as disclosed in U.S. Pat. Nos. 5,431,994, 5,318,735 and 5,281,378, all to Kozulla, and European Application No. 719 879 A2, all of which are incorporated above by reference. Another method of obtaining a skin-core structure involves employing a heated spinnerette to achieve thermal degradation of the filament surface, as disclosed in U.S. Pat. No. 5,705,119 to Takeuchi et al., and European Patent Application No. 0 630 996, all of which are incorporated above by reference. As discussed in U.S. patent application Ser. No. 08/728,491 to Harrington et al. and WO 97/37065, incorporated by reference as if set forth in their entirety herein, the skin-core structure can comprise a skin showing an enrichment of ruthenium staining of at least about 0.2 $\mu$m, more preferably at least about 0.5 $\mu$m, more preferably at least about 0.7 $\mu$m, even more preferably at least about 1 $\mu$m, and even more preferably at least about 1.5 $\mu$m.

With fibers having a denier less than 2 dpf, another manner of stating the ruthenium enrichment is with respect to the equivalent diameter of the fiber, wherein the equivalent diameter is equal to the diameter of a circle with equivalent cross-section area of the fiber averaged over five samples. More particularly, for fibers having a denier less than 2, the skin thickness can also be stated in terms of enrichment in staining of the equivalent diameter of the fiber. In such an instance, the enrichment in ruthenium staining can comprise at least about 1% and up to about 25% of the equivalent diameter of the fiber, preferably about 2% to 10% of the equivalent diameter of the fiber. Still further, the skin-core structure of the instant invention can be determined using a hot stage test, as disclosed in U.S. Pat. No. 5,705,119 to Takeuchi which is incorporated by reference herein, and a skin-core structure is present when a residue trail is present.

The skin-core structure comprises chemical modification of a filament to obtain the skin-core structure, and does not comprise separate components being joined along an axially extending interface, such as in sheath-core and side-by-side bicomponent fibers. Of course, the skin-core structure can be utilized in a composite fiber, such as the skin-core structure being present in the sheath of a sheath-core fiber in the manner disclosed in U.S. Pat. Nos. 5,281,378, 5,318,735 and 5,431,994 and EP Application No. 719 879 A2, which were discussed above and incorporated herein.

Thus, skin-core fibers can be prepared by providing conditions in any manner so that during extrusion of the polymer blend a skin-core structure is formed. For example, the temperature of a hot extrudate, such as an extrudate exiting a spinnerette, can be provided that is sufficiently elevated and for a sufficient amount of time within an oxidative atmosphere in order to obtain the skin-core structure. This elevated temperature can be achieved using a number of techniques, such as disclosed in the above discussed patents to Kozulla, and in U.S. and foreign applications to Takeuchi et al., discussed above and incorporated herein.

For example, skin-core filaments can be prepared in the inventive system through the method of U.S. Pat. Nos. 5,281,378, 5,318,735 and 5,431,994 to Kozulla, and European Patent Application No. 719 879 A2 in which the temperature of the hot extrudate can be provided above at least about 250° C. in an oxidative atmosphere for a period of time sufficient to obtain the oxidative chain scission degradation of its surface. This providing of the temperature can be obtained by delaying cooling of the hot extrudate as it exits the spinnerette, such as by blocking the flow of a quench gas reaching the hot extrudate. Such blocking can be achieved by the use of a shroud or a recessed spinnerette that is constructed and arranged to provide the maintaining of temperature.

In another aspect, as disclosed in U.S. Pat. No. 5,705,199 to Takeuchi et al., and European Patent Application No. 0 630 996, the skin-core structure can be obtained by heating the polymer blend in the vicinity of the spinnerette, either by directly heating the spinnerette or an area adjacent to the spinnerette. In other words, the polymer blend can be heated at a location at or adjacent to the at least one spinnerette, by directly heating the spinnerette or an element such as a heated plate positioned approximately 1 to 4 mm above the spinnerette, so as to heat the polymer composition to a sufficient temperature to obtain a skin-core fiber structure upon cooling, such as being immediately quenched, in an oxidative atmosphere.

In an application of the Takeuchi system to the present invention, for example, the extrusion temperature of the polymer may be about 230° C. to 250° C., and the spinnerette may have a temperature at its lower surface of preferably at least about 250° C. across the exit of the spinnerette in order to obtain oxidative chain scission degradation of the molten filaments to thereby obtain filaments having a skin-core structure. By the use of a heated spinnerette, therefore, the polymer blend is maintained at a sufficiently high temperature that upon extrusion from the spinnerette, oxidative chain scission occurs under oxidative quench conditions.

While the above techniques for forming the skin-core structure have been described, skin-core fibers prepared in the inventive system are not limited to those obtained by the above-described techniques. Any technique that provides a skin-core structure to the fiber is included in the scope of this invention.

In order to determine whether a skin-core fiber is present, a ruthenium staining test is utilized. As is disclosed in the above-noted U.S. and European applications to Takeuchi et al., which are incorporated by reference herein in their entirety, the substantially non-uniform morphological structure of the skin-core fibers according to the present invention can be characterized by transmission electron microscopy (TEM) of ruthenium tetroxide ($RuO_4$)-stained fiber thin sections. In this regard, as taught by Trent et al., in Macromolecules, Vol. 16, No. 4, 1983, "Ruthenium Tetroxide Staining of Polymers for Electron Microscopy", which is hereby incorporated by reference in its entirety, it is well known that the structure of polymeric materials is dependent on their heat treatment, composition, and processing, and that, in turn, mechanical properties of these materials such as toughness, impact strength, resilience, fatigue, and fracture strength can be highly sensitive to morphology. Further, this article teaches that transmission electron microscopy is an established technique for the characterization of the structure of heterogeneous polymer systems at a high level of resolution; however, it is often necessary to enhance image contrast for polymers by use of a staining agent. Useful staining agents for polymers are taught to include osmium tetroxide and ruthenium tetroxide. For the staining of the fibers of the present invention, ruthenium tetroxide is the preferred staining agent.

In the morphological characterization of the present invention, samples of fibers are stained with aqueous $RuO_4$, such as a 0.5% (by weight) aqueous solution of ruthenium tetroxide obtainable from Polysciences, Inc., overnight at room temperature. (While a liquid stain is utilized in this procedure, staining of the samples with a gaseous stain is also possible.) Stained fibers are embedded in Spurr epoxy resin and cured overnight at 60° C. The embedded stained fibers are then thin sectioned on an ultramicrotome using a diamond knife at room temperature to obtain microtomed sections approximately 80 nm thick, which can be examined on conventional apparatus, such as a Zeiss EM-10 TEM, at 100 kV. Energy dispersive x-ray analysis (EDX) was utilized to confirm that the $RuO_4$ had penetrated completely to the center of the fiber.

According to the present invention, the ruthenium staining test would be performed to determine whether a skin-core structure is present in a fiber. More specifically, a fiber can be subjected to ruthenium staining, and the enrichment of ruthenium (Ru residue) at the outer surface region of the fiber cross-section would be determnined. If the fiber shows an enrichment in the ruthenium staining for a thickness of at least about 0.2 $\mu$m or at least about 1% of the equivalent diameter for fibers having a denier of less than 2, the fiber has a skin-core structure.

While the ruthenium staining test is an excellent test for determining skin-core structure, there may be certain instances wherein enrichment in ruthenium staining may not occur. For example, there may be certain components within the fiber that would interfere with or prevent the ruthenium from showing an enrichment at the skin of the fiber, when, in fact, the fiber comprises a skin-core structure. The description of the ruthenium staining test herein is in the absence of any materials and/or components that would prevent, interfere with, or reduce the staining, whether these materials are in the fiber as a normal component of the fiber, such as being included therein as a component of the processed fiber, or whether these materials are in the fiber to prevent, interfere with or reduce ruthenium staining.

As discussed above, the present invention utilizes nonwoven materials including the fibers described above which are thermally bonded together. In particular, by incorporating the skin-core fibers described above into nonwoven materials, the resulting nonwoven materials possess exceptional cross-directional strength, softness and elongation properties. These nonwoven materials can be used as at least one layer in various products, including hygienic products, such as sanitary napkins, incontinence products and diapers, comprising at least one liquid absorbent layer and at least one nonwoven material layer of the present invention and/or incorporating fibers of the present invention thermally bonded together. Further, as previously indicated, the articles according to the present invention can include at least one liquid permeable or impermeable layer. For example, a diaper incorporating a nonwoven fabric of the present invention would include, as one embodiment, an outermost impermeable or permeable layer, an inner layer of the nonwoven material, and at least one intermediate absorbent layer. Of course, a plurality of nonwoven material layers and absorbent layers can be incorporated in the diaper (or other hygienic product) in various orientations, and a plurality of outer permeable and/or impermeable layers can be included for strength considerations.

Further, the nonwovens of the present invention can include a plurality of layers, with the layers being of the same fibers or different. Further, not all of the layers need include skin-core fibers of the polymer blend described above. For example, the nonwovens of the present invention can be used by themselves or in combination with other nonwovens, or in combination with other nonwovens or films.

Examples of suitable fibers are the following which are skin-core polypropylene fibers available from Hercules Incorporated, a Delaware corporation: T190 fiber which is a 2.2 dpf (denier-per-filament) staple fiber; T194 fiber which is a 2.6 dpf staple fiber; and T198 fiber which is a 2.6 dpf staple fiber.

The web may be a carded fibrous web or formed from continuous filaments and microfiber network structures, or from any of the many known conventional methods. The fibers can be formed in accordance with the process disclosed in co-pending U.S. application Ser. No. 08/728,491, filed Oct. 9, 1996, and WO 97/37065, the entire disclosures of which are expressly incorporated herein by reference.

Further, the fibers of the present invention can have any cross-sectional configuration, such as oval, circular, diamond, delta, trilobal—"Y"-shaped, "X"-shaped, and concave delta, wherein the sides of the delta are slightly concave. Preferably, the fibers include a circular or a concave delta cross-section configuration. The cross-sectional shapes are not limited to these examples, and can include other cross-sectional shapes. Additionally, the fibers can include hollow portions, such as a hollow fiber, which can be produced, for example, with a "C" cross-section spinnerette.

EXAMPLES

The invention generally described above is now further described with the following Examples. These Examples are meant to be illustrative of some embodiments of the invention, but are not meant to limit the invention in any way. Other embodiments, both as apparent to those in the art and as described above, are included in this invention, which is limited only by the claims. Unless otherwise noted, parts and percentages, etc., are by weight.

In the examples, normalized cross-directional strength and elongation were determined using test strips (six per sample) of each nonwoven, 1 inch×7 inches (25 mm×178 mm) using a tensile tester Model 1122 from Instron Corporation, Canton, Mass. Specifically, the breaking load and elongation are determined in accordance with the "cut strip test" in ASTM D-1682-64 (Re-approved 1975), which is incorporated by reference in its entirety, using the Instron Tester set at constant rate of traverse testing mode. The gauge length is 12.7 cm, the crosshead speed is 12.7 cm/minute, and the extension rate is 100%/minute.

Nonwoven fabrics were prepared by carding the fibers into conventional fiber webs at 250 feet per minute (76 m/min) using equipment and procedures as discussed in Legare, R. J., 1986 TAPPI Synthetic Fibers for Wet System and Thermal Bonding Applications, Boston Park Plaza Hotel & Towers, Boston, Mass. Oct. 9–10, 1986, "Thermal Bonding of Polypropylene Fibers in Nonwovens", pages 1–13, 57–71 and attached Tables and Figures. The Webmaster® randomizers described in the TAPPI article were not used. This article is incorporated herein in its entirety, by reference thereto.

Two layers of the carded staple fibers were stacked in the machine direction, and bonded using either a calender roll according to the present invention (identified as Roll B in Tables I–III), and a known diamond design embossed calender roll (identified as Roll A in Tables I–III) and a smooth roll at roll temperatures ranging from about 145 to 170° C. and roll pressures of 420 Newtons per linear centimeter (240 pounds per linear inch) to obtain nonwovens weighing nominally about 23.9 grams per square meter (20±1 grams per square yard).

Figure 12:
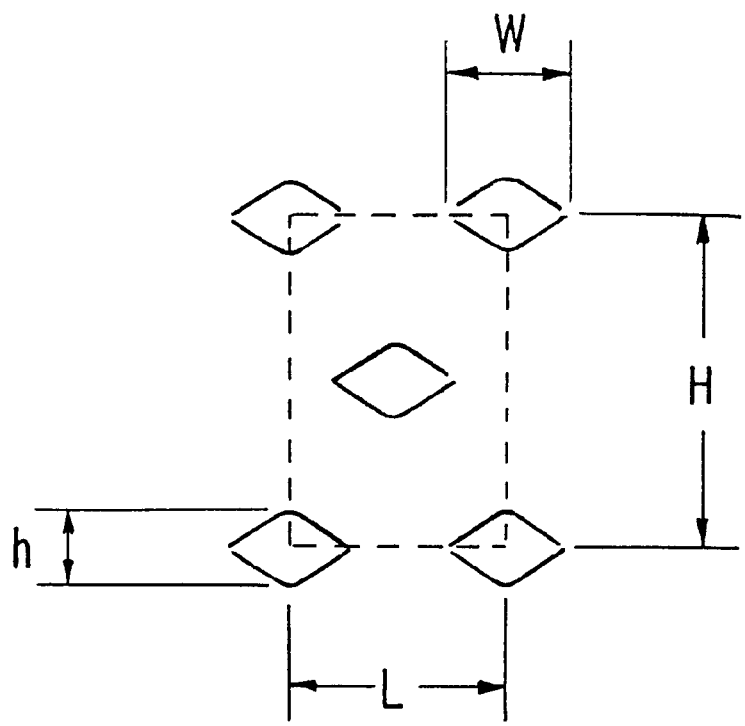
FIG. 12 is a schematic depiction of the land pattern of a prior art calender roll.

The diamond pattern calender roll had a 15% land area, 58.8 spots/sq.cm. with a depth of 0.076 cm. Further, the diamonds had a width (w) of 0.101 cm, a height (h) of 0.051 cm, and are spaced height-wise (H) 0.22 cm on center, and width-wise (L) 0.152 cm on center, as illustrated in FIG. 12.

The calender roll configured in accordance with the present invention (Roll B) was formed of ANSI 1030 engravable steel which was engraved to provide a plurality of lands, and ground in a cylindrical grinder to provide a minimum loss of outer diameter of the roll while keeping the roll concentric. Next the roll was polished to deburr and finished to 4–6 RMS. The resulting roll had a nominal diameter of approximately 24.65 cm and a length of about 57.15 cm, and the outer cylindrical surface included a plurality of lands having a truncated pyramidal shape, with a land or bond area of approximately 11% and 22 spots/sq.cm. Further, each truncated pyramidal shaped land had a rectangular base having a short side width (aligned in the machine or radial direction of the roll) of 0.107 cm, a long side length (aligned in the cross or longitudinal direction of the roll) of 0.158 cm, and a height of 0.76 cm. The upper surface of each land had short sides of 0.51 cm that extend parallel to the width of the base and had long sides of 0.102 cm that extend parallel to the length of the base. The sides of the lands tapered from the base to the upper surface at an angle of 20°.

The lands were provided on the outer peripheral surface and arranged in rows parallel to the longitudinal axis of the roll, and included 178 rows of 263 lands (short rows) alternating with 179 rows of 274 lands (long rows), respectively. The centers of the endmost lands in the short rows were spaced 2.007 cm from the roll ends, while the centers of the endmost lands in the long rows were spaced 0.244 cm from the roll ends. The centers of the lands of adjacent rows were spaced apart a distance of 0.224 cm (in the radial direction) and the distance from the center of a land in one row to the center of a land in an adjacent row (in the longitudinal direction of the roll) was 0.102 cm. Also, the distance between the bases in adjacent rows (in the radial direction) was 0.117 cm while the distance between bases in adjacent rows (in the longitudinal direction) was 0.046 cm.

Figure 5:
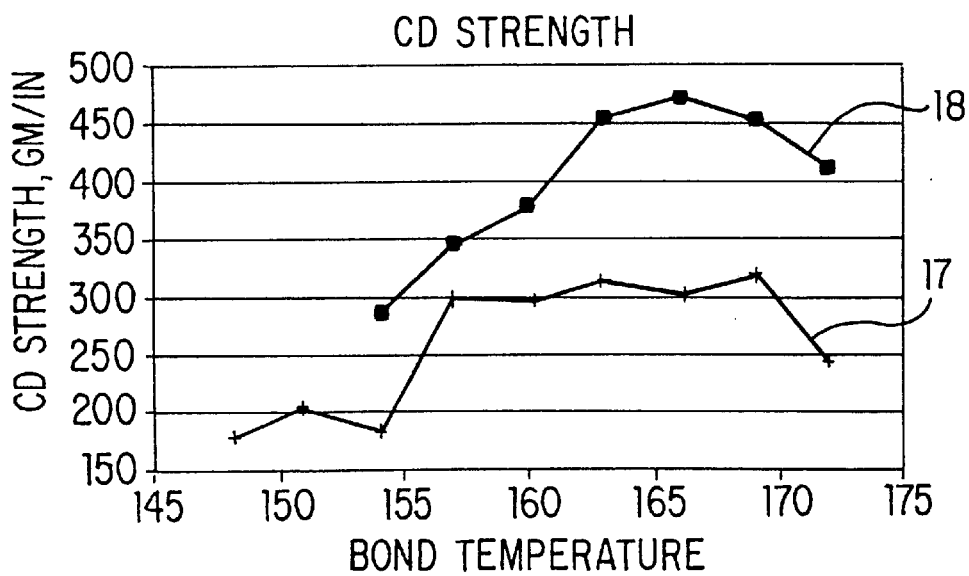
FIG. 5 is a graphical comparison of the cross-directional strength of a thermal bonded fabric formed of a first fiber according to a prior art patterned calender roll and the patterned calender roll of the present invention.
Figure 6:
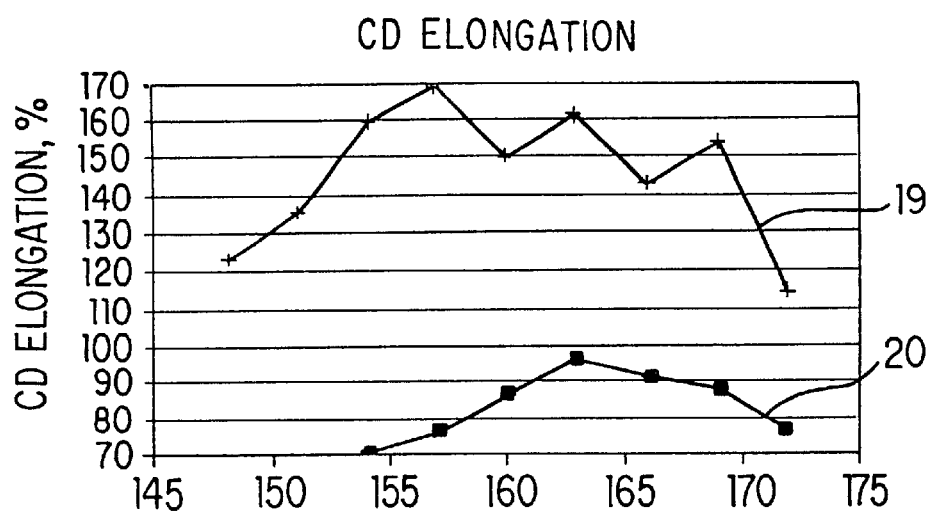
FIG. 6 is a graphical comparison of the cross-directional elongation of the fabrics formed from the first fiber.
Figure 7:
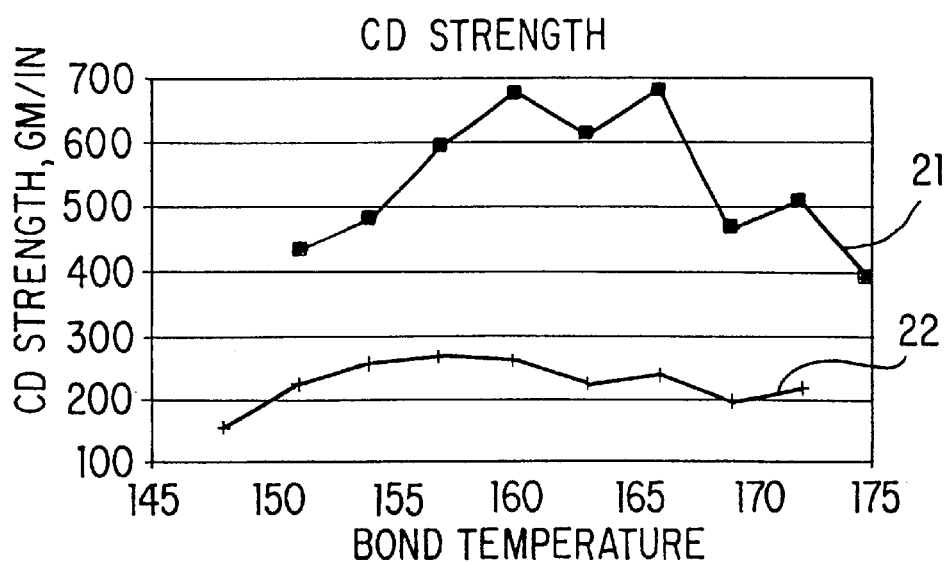
FIG. 7 is a graphical comparison of the cross-directional strength of a thermal bonded fabric formed of a second fiber according to a prior art patterned calender roll and the patterned calender roll of the present invention.
Figure 8:
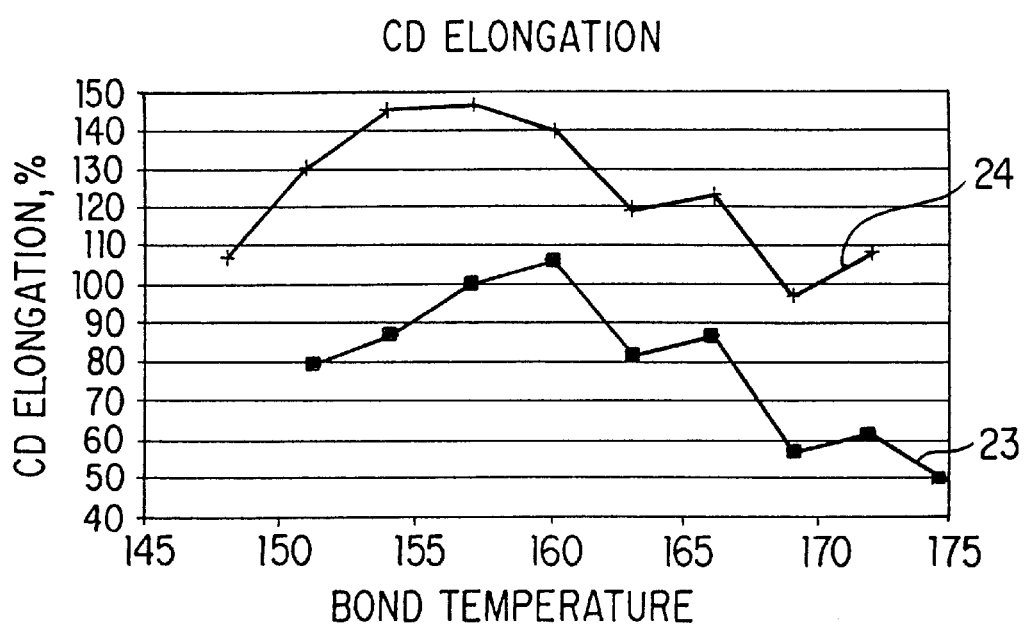
FIG. 8 is a graphical comparison of the cross-directional elongation of the fabrics formed from the second fiber.
Figure 9:
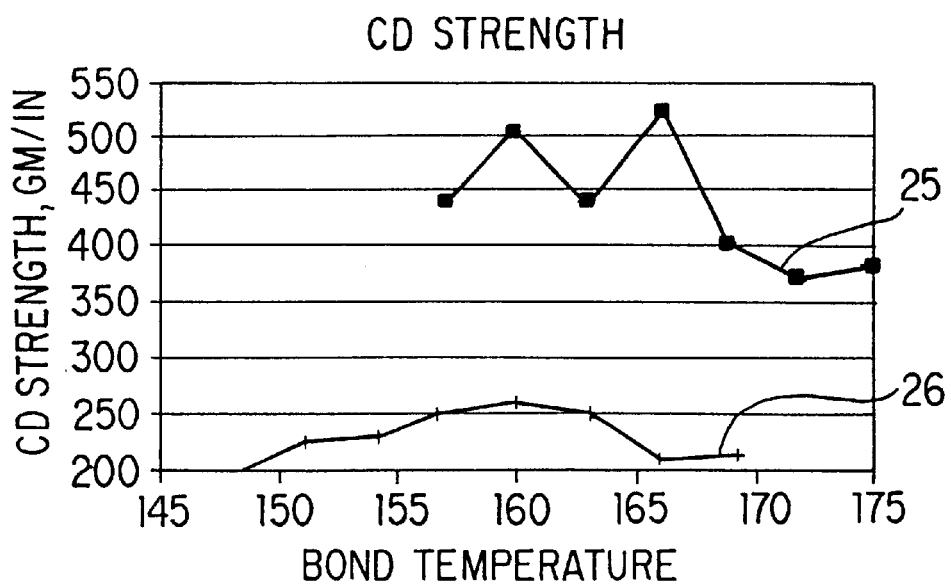
FIG. 9 is a graphical comparison of the cross-directional strength of a thermal bonded fabric formed of a third fiber according to a prior art patterned calender roll and the patterned calender roll of the present invention.
Figure 10:
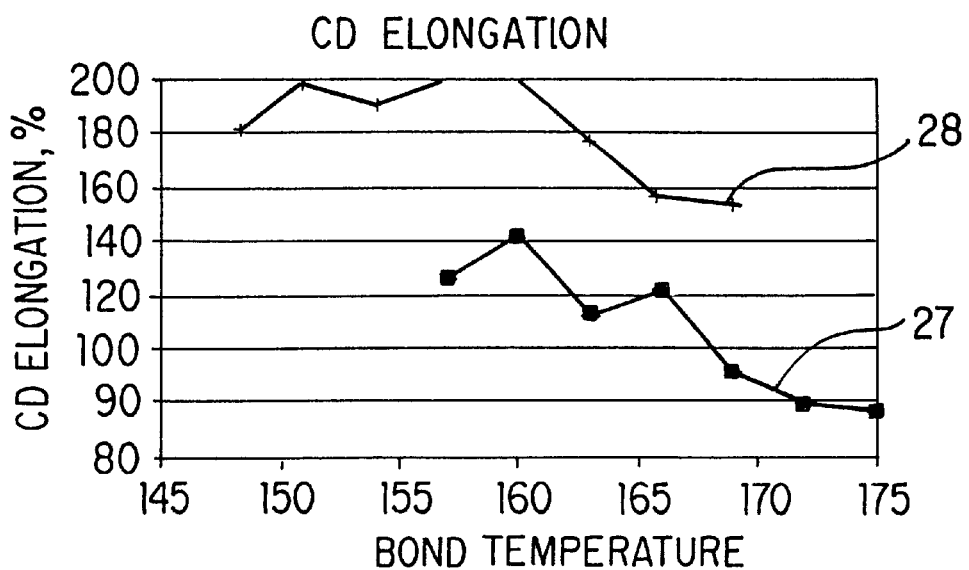
FIG. 10 is a graphical comparison of the cross-directional elongation of the fabrics formed by the third fiber.

The increased stretch or elongation of the thermal bonded skin-core polypropylene fabric formed in accordance with the present invention is demonstrated in Tables I–III and corresponding FIGS. 5–10 . Tables I–III compare the cross-directional strength (CDS) and cross-directional elongation (CDE) of fabrics formed of three different fibers, with each table comparing a fabric formed with a conventional patterned roll (Roll A) and with a patterned roll according to the present invention (Roll B). As shown in Table 1 for a T190 fiber with 2.2 DPF, and as depicted in FIGS. 5 and 6, the cross-directional strength for a fabric formed from a calender roll according to the present invention (curve 17) is somewhat less than that formed by the conventional calender roll (curve 18). However, and importantly, the cross-directional elongation of the fabric formed in accordance with the present invention (curve 19) has greatly increased elongation as compared to that formed by the conventional calender roll (curve 20).

TABLE I

T190 2.2 DPF FIBER

| BOND TEMP ° C. | Roll A CDS | Roll B CDS | Roll A CDE | Roll B CDE |
| --- | --- | --- | --- | --- |
| 148 |  | 178 |  | 123 |
| 151 |  | 204 |  | 135 |
| 154 | 285 | 184 | 71 | 159 |
| 157 | 343 | 298 | 76 | 169 |
| 160 | 375 | 294 | 86 | 150 |
| 163 | 454 | 314 | 96 | 162 |
| 166 | 472 | 302 | 91 | 143 |
| 169 | 452 | 319 | 87 | 154 |
| 172 | 412 | 242 | 76 | 114 |

Turning to the Table II data which is for a T198 fiber with 2.6 DPF, and the Table III data which is for a T194 fiber with a 2.6 DPF, similar results can be seen when comparing the fabric formed with these fibers by the conventional calender roll A (curves 21, 23, 25 and 27 as depicted in FIGS. 7–10) when compared with the patterned roll B according to the present invention (curves 22, 24, 26, 28 as depicted in FIGS. 7–10).

TABLE II

T198 2.6 DPF FIBER

| BOND TEMP ° C. | Roll A CDS | Roll B CDS | Roll A CDE | Roll B CDE |
| --- | --- | --- | --- | --- |
| 148 |  | 154 |  | 107 |
| 151 | 431 | 226 | 79 | 131 |
| 154 | 480 | 255 | 87 | 146 |
| 157 | 594 | 267 | 100 | 147 |
| 160 | 672 | 261 | 106 | 140 |
| 163 | 609 | 223 | 82 | 119 |
| 166 | 679 | 236 | 87 | 124 |
| 169 | 463 | 191 | 57 | 97 |

TABLE II-continued

T198 2.6 DPF FIBER

| BOND TEMP °C. | Roll A CDS | Roll B CDS | Roll A CDE | Roll B CDE |
|---|---|---|---|---|
| 172 | 502 | 214 | 62 | 108 |
| 175 | 382 |  | 49 |  |

TABLE III

T194 2.6 DPF FIBER

| BOND TEMP °C. | Roll A CDS | Roll B CDS | Roll A CDE | Roll B CDE |
|---|---|---|---|---|
| 148 |  | 200 |  | 180 |
| 151 |  | 226 |  | 199 |
| 154 |  | 231 |  | 190 |
| 157 | 439 | 250 | 125 | 199 |
| 160 | 506 | 259 | 142 | 200 |
| 163 | 439 | 252 | 111 | 178 |
| 166 | 525 | 210 | 121 | 154 |
| 169 | 400 | 216 | 89 | 151 |
| 172 | 371 |  | 78 |  |
| 175 | 382 |  | 76 |  |

Accordingly, it can be seen that by using the calender roll having the pattern of lands according to the present invention in the method according to the present invention and utilizing skin-core polypropylene fibers result in a thermal bonded fabric having a much greater stretchability or elongation than that of thermal bonded fabrics formed with a roller having a conventional pattern.

Although the invention has been described herein with reference to particular means, materials and embodiments, the invention is not intended to be limited to the particulars disclosed herein; rather, the invention extends to all fuinctionally equivalent structures, methods and uses, such as are within the scope of the appended claims.

What is claimed is:

1. A method of manufacturing thermally bonded fabric, the method comprising:
   forming a web of thermally bondable polypropylene fibers;
   passing said web over a heated calender roll having a patterned surface including a plurality of rows of lands, with each of said lands having an upper surface, with upper surfaces of lands in adjacent rows of lands being staggered such that they do not overlap one another in a machine direction; and
   thermally bonding the fibers at bond points located about the upper surfaces of the lands such that fibers extending in the machine direction or substantially in the machine direction will only have one bond point for adjacent rows of lands.

2. The method according to claim 1, wherein said polypropylene fibers are skin core polypropylene fibers.

3. The method according to claim 2, further comprising providing the web as a carded fibrous web.

4. The method according to claim 2, further comprising providing the web as a plurality of continuous filaments.

5. The method according to claim 2, wherein said elongation is at least about 120%.

6. The method according to claim 5, wherein said elongation is greater than about. 140%.

7. The method according to claim 6, wherein said elongation is greater than about 160%.

8. The method according to claim 7, wherein said elongation is greater than about 180%.

9. The method according to claim 8, wherein said elongation is greater than about 200%.

10. The method according to claim 9, wherein said elongation is greater than about 250%.

11. The method according to claim 10, wherein said elongation is greater than about 300%.

12. The method according to claim 2, wherein the passing said web over a heated calender roll comprises:
    passing said fibrous web between a pair of cooperating rolls in a calender nip, at least one of said pair of rolls having said patterned surface and comprising a cylindrical roll having an outer cylindrical surface including a plurality of lands;
    said lands being arranged on said outer cylindrical surface in a plurality of spaced apart rows;
    each of said lands comprising a tapered shape including a base tapering to an upper surface;
    said upper surface including short sides of about 0.036 cm to 0.066 cm in length oriented in a machine direction and long sides of about 0.071 cm to 0.133 cm in length oriented in a cross direction;
    adjacent rows of said lands being spaced apart a distance, with respect to the centers of said lands, of about 0.157 cm to 0.291 cm;
    upper surfaces of lands in adjacent rows being staggered such that upper surfaces in adjacent rows do not overlap with one another in a machine direction providing a plurality of spaced apart bond points capable of bonding fibers extending in the machine direction or substantially in the machine direction at only one bond point for adjacent rows; and
    said plurality of lands providing a bond area up to about 20%.

13. The method according to claim 12, wherein said upper surfaces are substantially rectangular.

14. The method according to claim 13, wherein said bases overlap in the machine direction in adjacent rows.

15. The method according to claim 14, wherein said bond area ranges from about 5% to 20%.

16. The method according to claims 15, wherein said bond area is in the range of about 8% to about 12%.

17. The method according to claim 16, wherein said bond area is about 11%.

18. The method according to claim 15, wherein said bond area is in the range of about 8% to about 15%.

19. The method according to claim 18, wherein centers of said lands in each row are spaced apart by a distance of about 0.142 cm to 0.264 cm, and centers of said lands in adjacent rows are spaced apart by a distance of about 0.071 cm to 0.133 cm.

20. The method according to claim 18, wherein said lands are constructed and arranged such that a straight fiber lying at an angle of about 35° to 55° with respect to the machine direction is positioned in a space between said lands, whereby the fiber is not bonded.

21. The method according to claim 20, wherein said lands are constructed and arranged such that a straight fiber lying at an angle of about 45° with respect to the machine direction is positioned in a space between said lands, whereby the fiber is not bonded.

22. The method according to claim 18, wherein said lands are of a truncated pyramidal shape, each having a substantially rectangular base with short sides about 0.075 cm to 0.139 cm in length oriented in the machine direction and long sides about 0.111 cm to 0.205 cm in length oriented in the cross direction, and tapered side walls extending between the base and the upper surface at an angle α of about 14° to 35°.

23. The method according to claim 22, wherein said tapered side walls extend between the base and the upper surface at an angle a of about 17° to 23°.

24. The method according to claim 18, wherein:
   said lands are of a truncated pyramidal shape having an upper surface with short sides of about 0.043 cm to 0.059 cm in length oriented in a machine direction and long sides of about 0.087 cm to 0.117 cm in length oriented in a cross direction;
   adjacent rows of said lands being spaced apart a distance, with respect to the centers of said lands, of about 0.190 cm to 0.258 cm;
   centers of said lands in each row are spaced apart by a distance of about 0.173 cm to 0.233 cm, and centers of said lands in adjacent rows are spaced apart by a distance of about 0.087 cm to 0.117 cm;
   said lands are constructed and arranged such that a straight fiber lying at an angle of about 45° with respect to the machine direction is positioned in a space between said lands, whereby the fiber is not bonded; and
   said truncated pyramidal shape lands each have a substantially rectangular base with short sides about 0.091 cm to 0.123 cm in length oriented in the machine direction and long sides about 0.134 to 0.182 cm in length oriented in the cross directi6n, and tapered side walls extending between the base and the upper surface at an angle a of about 17° to 26°.

25. The method according to claim 18, wherein:
   each of said lands comprising a truncated pyramidal shape having an upper surface with short sides of about 0.051 cm in length oriented in a machine direction and long sides of about 0.102 cm in length oriented in a cross direction;
   adjacent rows of said lands being spaced apart a distance, with respect to the centers of said lands, of about 0.224 cm;
   centers of said lands in each row are spaced apart by a distance of about 0.203 cm, and centers of said lands in adjacent rows are spaced apart by a distance of about 0.102 cm;
   said lands are constructed and arranged such that a straight fiber tying at an angle of about 45° with respect to the machine direction is positioned in a space between said lands, whereby the fiber is not bonded; and
   said truncated pyramidal shape lands each have a substantially rectangular base with short sides about 0.107 cm in length oriented in the machine direction and long sides about 0.158 cm in length oriented in the cross direction, and tapered side walls extending between the base and the upper surface at an angle α of about 17° to 23°.

26. A method of manufacturing thermally bonded fabric, the method comprising:
   forming a web comprising thermally bondable skin-core polypropylene fibers;
   passing said web over a calender roll having a patterned surface including a plurality of rows of lands, with each of said lands having an upper surface, with upper surfaces of lands in adjacent rows of lands being staggered such that they do not overlap one another in a machine direction;
   applying heat and pressure to said fibrous web at a location of said calender roll to thermally bond the fibers at bond points located about the upper surfaces of the lands such that fibers extending in the machine direction or substantially in the machine direction will only have one bond point for adjacent rows of lands.

\* \* \* \* \*